(12) United States Patent
Zhong et al.

(10) Patent No.: US 7,422,760 B2
(45) Date of Patent: Sep. 9, 2008

(54) PLANT-BASED MEDICAMENT FOR THE TREATMENT OF HEPATITIS C

(75) Inventors: Shouming Zhong, Oxford (GB); Hongwen Yu, Oxford (GB)

(73) Assignee: Phynova Limited (GB)

( * ) Notice: Subject to any disclaimer, the term of this patent is extended or adjusted under 35 U.S.C. 154(b) by 0 days.

(21) Appl. No.: 10/589,738

(22) PCT Filed: Feb. 17, 2005

(86) PCT No.: PCT/GB2005/000559

§ 371 (c)(1), (2), (4) Date: Aug. 16, 2006

(87) PCT Pub. No.: WO2005/079823

PCT Pub. Date: Sep. 1, 2005

(65) Prior Publication Data

US 2007/0160693 A1    Jul. 12, 2007

(30) Foreign Application Priority Data

Feb. 19, 2004    (GB) ................ 0403708.1

(51) Int. Cl.
*A61K 36/537* (2006.01)
*A61K 36/00* (2006.01)

(52) U.S. Cl. .............. 424/746; 424/773; 424/777; 424/725

(58) Field of Classification Search .......... None
See application file for complete search history.

(56) References Cited

U.S. PATENT DOCUMENTS

| 6,043,276 A | 3/2000 | Han et al. |
| 6,126,942 A * | 10/2000 | Yang ............ 424/728 |
| 6,455,078 B1 * | 9/2002 | Wu ............ 424/725 |
| 2002/0102237 A1 * | 8/2002 | Hammerly ............ 424/85.5 |

FOREIGN PATENT DOCUMENTS

| CN | 1071581 A | 5/1993 |
| CN | 1151312 A | 6/1997 |
| CN | 1183288 A | 6/1998 |
| CN | 1053375 C | 6/2000 |
| CN | 1053825 C | 6/2000 |
| CN | 1371713 A | 10/2002 |
| CN | 1393255 A | 1/2003 |
| CN | 1418637 | 5/2003 |
| GB | 2 411 114 A | 8/2005 |
| JP | 2001/39868 | 2/2001 |
| WO | WO 02/32444 | 4/2002 |
| WO | WO 2005/000559 | 2/2005 |

OTHER PUBLICATIONS

Mary L. Chaves, PharmD, "Treatment of Hepatitis C with Milk Thistle?" Journal of Herbal Pharmacotherapy, vol. 1(3) 2001, pp. 79 and 86-90, Published in Glendale, Arizona.
Edward Fogden and James Neuberger, "Alternative Medicines and the Liver" Liver International; 2003, pp. 213-220, Published in Denmark.
Abstracts: Autoimmune Cholangitis Manifesting as Cutaneous Lymphocytic Vasculitis of the Lower Extremities, Alex R. Rusynyk, D.O., 2002 pp. 273-276, Published in Danville, PA.

* cited by examiner

*Primary Examiner*—Christopher R. Tate
(74) *Attorney, Agent, or Firm*—Dickinson Wright PLLC

(57) ABSTRACT

The present invention relates to a botanical drug or dietary supplement for use in the treatment of patients suffering from Hepatitis C virus infection. More particularly, it relates to a botanical drug consisting essentially of four botanical drug substances, optionally formulated with excipients, for use either in alleviating the symptoms of Hepatitis, particularly chronic Hepatitis C, and/or inhibiting the activity of the causative Hepatitis C virus. The botanical raw materials, botanical drug substances or botanical ingredients used are from a species of each of the genera: (a) *Silybum*; (b) *Astragalus* or *Hedysarum*; (c) *Salvia*; and (d) *Schisandra*.

34 Claims, 13 Drawing Sheets

Peak Results (Volume 20.00, Run Time 40.0mins)

| Name | Ret Time (min) | Area (uV*sec) | Height (uV) | Amount | Units |
|---|---|---|---|---|---|
| Astragloside | 19.800 | 2555387 | 4303 | 12.414 | ug |

Peak Results (Volume 20.00, Run Time 40.0mins)

| Name | Ret Time (min) | Area (uV*sec) | Height (uV) | Amount | Units |
|---|---|---|---|---|---|
| Schisandrin | 14.550 | 1110494 | 20832 | 2.329 | ug |

PLANT-BASED MEDICAMENT FOR THE TREATMENT OF HEPATITIS C

CROSS REFERENCE TO RELATED APPLICATIONS

This application claims the benefit of PCT International Application No. PCT/GB2005/000559 filed Feb. 17, 2005, which in turn claims priority from Great Britain Application No. 0 403 708.1 filed Feb. 19, 2004.

TECHNICAL FIELD

The present invention relates to a botanical drug or dietary supplement for use in the treatment of patients suffering from Hepatitis C virus infection. More particularly, it relates to a botanical drug consisting essentially of four botanical drug substances, optionally formulated with excipients, for use either in alleviating the symptoms of Hepatitis, particularly chronic Hepatitis C, and/or inhibiting the activity of the causative Hepatitis C virus.

BACKGROUND OF THE INVENTION

Chronic infection with the Hepatitis C virus (HCV) is common, affecting up to 1% of the UK population. It is well recognised that chronic HCV infection is associated with a wide variety of symptoms including fatigue, upper abdominal pain and dyspepsia, which lead to an overall reduction in the quality of life. Conventional therapy with pharmaceutical agents leads to an improvement in symptoms but is effective in only 40% of patients. There is thus a need for effective treatments that can reduce the symptoms associated with chronic Hepatitis C virus (HCV) infection and thereby improve the quality of life of a greater percentage of HCV patients.

DEFINITIONS

In the specification the following definitions, taken from the U.S. Department of Health and Human Services, Food and Drug Administration, Center for Drug Evaluation and Research (CDER), Aug. 2000 Guidance for Industry, Botanical Drug Products, are intended:

Active Constituent: The chemical constituent in a botanical raw material, drug substance, or drug product that is responsible for the intended pharmacological activity or therapeutic effect.

Botanical Product; Botanical: A finished, labelled product that contains vegetable matter, which may include plant materials (see below), algae, macroscopic fungi, or combinations of these. Depending in part on its intended use, a botanical product may be a food, drug, medical device, or cosmetic.

Botanical Drug Product; Botanical Drug: A botanical product that is intended for use as a drug; a drug product that is prepared from a botanical drug substance. Botanical drug products are available in a variety of dosage forms, such as solutions (e.g., teas), powders, tablets, capsules, elixirs, and topicals.

Botanical Drug Substance: A drug substance derived from one or more plants, algae, or macroscopic fungi. It is prepared from botanical raw materials by one or more of the following processes: pulverization, decoction, expression, aqueous extraction, ethanolic extraction, or other similar process. It may be available in a variety of physical forms, such as powder, paste, concentrated liquid, juice, gum, syrup, or oil. A botanical drug substance can be made from one or more botanical raw materials (see Single-Herb and Multi-Herb botanical drug substance or product). A botanical drug substance does not include a highly purified or chemically modified substance derived from natural sources.

Botanical Ingredient: A component of a botanical drug substance or product that originates from a botanical raw material.

Botanical Raw Material: Fresh or processed (e.g., cleaned, frozen, dried, or sliced) part of a single species of plant or a fresh or processed alga or macroscopic fungus.

Chromatographic Fingerprint: A chromatographic profile of a botanical raw material or drug substance that is matched qualitatively and quantitatively against that of a reference sample or standard to ensure the identity and quality of a batch and consistency from batch to batch.

Dietary Supplement: [A] product (other than tobacco) intended to supplement the diet that bears or contains one or more of the following dietary ingredients: (A) a vitamin; (B) a mineral; (C) an herb or other botanical; (D) an amino acid; (E) a dietary substance for use by man to supplement the diet by increasing the total dietary intake; or (F) a concentrate, metabolite, constituent, extract, or combination of any ingredient described in clause (A), (B), (C), (D), or (E); (2) means a product that (A) is intended for ingestion in a form described in section 411(c)(1)(B)(i) [of the FD&C Act]; or complies with section 411(c)(1)(B)(ii); is not represented for use as a conventional food or as a sole item of a meal or the diet; and is labeled as a dietary supplement; and (3) does (A) include an article that is approved as a new drug under section 505 or licensed as a biologic under section 351 of the Public Health Service Act (42 U.S.C. 262) and was, prior to such approval, certification, or license, marketed as a dietary supplement or as a food unless [FDA] has issued a regulation, after notice and comment, finding that the article, when used as or in a dietary supplement under the conditions of use and dosages set forth in the labelling for such dietary supplement, is unlawful under section 402(f); and (B) not include (i) an article that is approved as a new drug under section 505, certified as an antibiotic under section 507, or licensed as a biologic under section 351 of the Public Health Service Act (42 U.S.C. 262), or (ii) an article authorized for investigation as a new drug, antibiotic, or biological for which substantial clinical investigations have been instituted and for which the existence of such investigations has been made public, which was not before such approval, certification, licensing, or authorization marketed as a dietary supplement or as a food unless [FDA], in [its] discretion, has issued a regulation, after notice and comment, finding that the article would be lawful under this Act_(21 U.S.C. 321(ff)).

Dosage Form: A pharmaceutical product type, for example, tablet, capsule, solution, or cream, that contains a drug ingredient (substance) generally, but not necessarily, in association with excipients.

Drug: Means (A) articles recognized in the official United States Pharmacopeia, official Homeopathic Pharmacopeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals; and (D) articles intended for use as a component of any articles specified in clause (A), (B), or (C). A food or dietary supplement for which a claim, subject to sections 403(r)(1)(B) and 403(r)(3) [of the FD&C Act] or sections 403(r)(1)(B) and (r)(5)(D), is made in accordance with the requirements of section 403(r) is not a drug solely because the label or the labeling contains such a claim.

A food, dietary ingredient, or dietary supplement for which a truthful and not misleading statement is made in accordance with section 403(r)(6) is not a drug under clause (C) solely because the label or the labelling contains such a statement_ (21 U.S.C. 321(g)(1)).

Drug Substance: An active ingredient that is intended to furnish pharmacological activity or other direct effect in the diagnosis, cure, mitigation, treatment, or prevention of disease or to affect the structure or any function of the human body (21 CFR 314.3(b)).

Drug Product: The dosage form in the final immediate packaging intended for marketing.

Food: The term food means (1) articles used for food or drink, (2) chewing gum, and (3) articles used for components of such articles (21 U.S.C. 321(f)).

Formulation: A formula that lists the components (or ingredients) and composition of the dosage form. The components and composition of a multi-herb botanical drug substance should be part of the total formulation.

Marker: A chemical constituent of a botanical raw material, drug substance, or drug product that is used for identification and/or quality control purposes, especially when the active constituents are not known or identified.

Multi-Herb (Botanical Drug) Substance or Product: A botanical drug substance or drug product that is derived from more than one botanical raw material, each of which is considered a botanical ingredient. A multi-herb botanical drug substance may be prepared by processing together two or more botanical raw materials, or by combining two or more single-herb botanical drug substances that have been individually processed from their corresponding raw materials. In the latter case, the individual single-herb botanical drug substances may be introduced simultaneously or at different stages during the manufacturing process of the dosage form.

Plant Material: A plant or plant part (e.g., bark, wood, leaves, stems, roots, flowers, fruits, seeds, berries, or parts thereof) as well as exudates.

Single-Herb (Botanical Drug) Substance or Product: A botanical drug substance or drug product that is derived from one botanical raw material. Therefore, a single-herb substance or product generally contains only one botanical ingredient.

In addition the terms:

Consisting essentially is intended to refer back only to the presence of the botanical raw materials and their derivatives and excludes the presence of e.g. excipients used in the formulation;

Treatment is intended to refer to both symptomatic relief and/or activity against the causative factor.

In Traditional Chinese Medicine (TCM), HCV infection is regarded as causing the following pathological changes in the body:

accumulation of toxin and heat in the blood;
consumption of vital energy and body fluid;
stagnation of blood; and
injury of liver and spleen function.

In order to address these different aspects existing TCM plant based formulations for HCV treatment usually contain many ingredients, typically ten or more. For practical purposes it would clearly be desirable and advantageous to minimise the number of botanical ingredients or botanical drug substances without in any way compromising therapeutic efficacy.

Surprisingly the applicant has found that a combination of only four plant species demonstrates activity against Hepatitis C virus.

DISCLOSURE OF THE INVENTION

According to a first aspect of the present invention there is provided a botanical drug or dietary supplement, for the treatment of or for use in patients with Hepatitis C infection, consisting essentially of botanical raw materials, botanical drug substances or botanical ingredients from a species of each of the genera:

(a) *Silybum;*
(b) *Astragalus* or *Hedysarum;*
(c) *Salvia;* and
(d) *Schisandra.*

The preferred species of each of the four botanical raw materials is set out below:

The *Silybum* species is typically *Silybum marianum*. Preferably the plant material of the *Silybum* species which is used in the composition of the invention is the fruit. The fruit of *Silybum marianum* is known in TCM as Sui Fei Ji and in Western Europe as milk thistle fruit.

The *Astragalus* species: is typically *Astragalus membranaceus* var *mongholicus*. Preferably the plant material of the *Astragalus* species which is used is the root. The root of *Astragalus membranaceus* var *mongholicus* is known in TCM as Huang Qi and in Western Europe as *Astragalus* root. As alternatives to *Astragalus membranaceus* var *mongholicus*, another *Astragalus* species, *A. membranaceus* or a *Hedysarum* species may be used. The preferred *Hedysarum* species is *Hedysarum polybotyrs*. The root of *Hedysarum polybotyrs* is known in TCM as Hong Qi. The *Astragalus* species and *Hedysarum* species disclosed in this application may be used interchangeably in TCM.

The *Salvia* species is typically *Salvia miltiorrhiza*. Preferably the plant material of the *Salvia* species which is used in the composition of the invention is the root. The root of *Salvia miltiorrhiza* is known in TCM as Dan Shen and in Western Europe as Chinese sage root. Alternatively *Salvia bowleyana* or *Salvia przewalskii* may be used. Similarly, the *Salvia* species disclosed in this application may be used interchangeably in TCM The *Schisandra* species is typically *Schisandra chinensis*. Preferably the plant material of the *Schisandra* species which is used in the composition of the invention is the fruit. The fruit of *Schisandra chinensis* is known in TCM as Wu Wei Zi, and in Western Europe as *Schisandra* fruit. Alternatively *Schisandra sphenanthera* may be used. Similarly, the *Schisandra* species disclosed in this application may be used interchangeably in TCM In a preferred embodiment the plant species are:

a) *Silybum marianum;*
b) *Astragalus membranaceus* var *mongholicus;*
c) *Salvia miltiorrhiza;* and
d) *Schisandra chinensis.*

In alternative embodiments the *Astragalus membranaceus* var *mongholicus* may be substituted with *Astragalus membranaceus* or *Hedysarum polybotyrs*.

A particularly preferred composition of the invention comprises: Sui Fei Ji; Dan Shen; Wu Wei Zi; and Huang Qi.

Whilst in a favoured embodiment the invention takes the form of a botanical drug, comprising or consisting essentially of botanical drug substances of each of the four plant species in further embodiments the botanical drug may comprise or consist essentially of botanical ingredients of each of the species. Where the product is a dietary supplement the four plant species may additionally be in the form of botanical raw materials.

In the case of a botanical drug there may be present, in addition to the botanical drug substances, pharmaceutically acceptable excipients.

In the case of a dietary supplement there may be present in addition to the botanical raw materials, botanical drug substances or botanical ingredients one or more dietetically acceptable excipients.

The present invention also provides a method of treatment or dietary supplementation which comprises administering to a human a composition of the invention in an amount sufficient to support healthy liver function and/or relieve the symptoms of Hepatitis C viral infection and/or to reduce viral load.

The plant materials may be employed in the composition of the invention in any suitable form. This may for instance be as crude plant material, which is either fresh or dried, or as an extract of fresh or dried plant material, i.e. a botanical drug substance. The extract is preferably a total plant extract defined with reference to one or more chemical markers although defined fractions and botanical ingredients may also be used. The extract, most usually a botanical drug substance, is typically dried and used in powder form, most preferably as a lyophilised extract.

When botanical drug substance is used it is preferably pulverized. In this embodiment the botanical drug substance is dried and ground to a powder. The resulting powder of the or each botanical drug substance is then conveniently mixed together to form a plant based composition of the invention in powder form. This powder can be administered directly, for instance by being dispersed in a liquid for human subjects to drink. Alternatively the powder can be processed into any other conventional dosage form such as capsules, tablets or granules. In a preferred embodiment the applicant has developed a suspension formulation which is suspendable in a relatively small volume of a cold liquid, such as water. Typically the suspension formulation can be suspended in less than 50 ml, more typically less than 25 ml of water. Preferably the packaged medicament is supplied with a dispensing container.

A botanical drug substance, for instance a total extract, may be prepared by any conventional technique known for the extraction of ingredients from botanical materials. These include solvent extraction including supercritical fluid extraction using a liquefied gas such as carbon dioxide. In one embodiment the extracts are ethanolic extracts, such as those obtained using 70% ethanol. The extracts are most preferably standardised extract, for instance a standardised total extract. The preferred standardised total extracts are pharmaceutical grade extracts.

An extract is typically prepared by immersing or macerating or refluxing fresh or dry plant material, for instance powdered dry plant material, in a suitable solvent; separating solid residue from the solution, removing the solvent from the solution; and recovering the resulting concentrates.

If desired a liquid extract may be dried before being formulated into a botanical drug or dietary supplement of the invention, for instance by spray drying or by freeze drying (lyophilisation). In that case the dried extract of one or more of the constituent plant species of the composition of the invention may be mixed with pulverized dried plant material of one or more of the other constituent plant species, to form a powder for direct administration to human subjects or for encapsulation or tabletting into unit dosage forms. Alternatively the extract may be used directly without prior drying.

The botanical raw materials or botanical drug substances or botanical ingredients may be combined together using any conventional technique that is suitable for ingredients of this type. When the botanical raw materials, drug substances or botanical ingredients are all in dry form they are conveniently mixed together, for instance by hand or by means of a mechanical mixer. A mixing procedure of this type may also be suitable if some, but not all, of the components of the plant based composition are in dry form.

The *Silybum marianum* is preferably employed in the form of a pharmaceutical grade extract that can be obtained commercially from, for example, an Italian manufacturer, Indena. The pharmaceutical grade *Silybum marianum* extract manufactured by Indena is standardized for silymarin content of no less than 30% weight percent by HPLC. The pharmaceutical grade extract must pass extensive safety and efficacy procedures. Preferably, when employed in the practice of the present invention the *Silybum marianum* extract has a minimum silymarin content of at least 30% by HPLC analysis.

The *Astragalus membranaceus* var *mongholicus* is preferably employed in the form of a pharmaceutical grade extract that can be obtained commercially from, for example, a Chinese manufacturer, the Institute of Medicinal Plant Development, Haiding District, Xibeiwang, Beijing 100094, China. Pharmaceutical grade *Astragalus membranaceus* var *mongholicus* extract manufactured in China is standardized for an Astragaloside IV content of about 0.4 weight percent. The pharmaceutical grade extract must pass extensive safety and efficacy procedures. Preferably, when employed in the practice of the present invention the *Astragalus membranaceus* var *mongholicus* extract has an Astragaloside IV content of from 0.1 to about 10 weight percentage. Preferably, the *Astragalus membranaceus* var *mongholicus* extract used in the present invention has a minimum Astragaloside IV content of at least 0.4 percent.

The *Salvia miltiorrhiza* is preferably employed in the form of a pharmaceutical grade extract that can be obtained commercially from, for example, a Chinese manufacturer, the Institute of Medicinal Plant Development, Haiding District, Xibeiwang, Beijing 100094, China. Pharmaceutical grade *Salvia miltiorrhiza* extract manufactured in China is standardized for a Tanshinone IIa content of about 1.5 weight percent. The pharmaceutical grade extract must pass extensive safety and efficacy procedures. Preferably, when employed in the practice of the present invention the *Salvia miltiorrhiza* extract has a Tanshinone IIa content of from 1.5 to about 50% weight percentage. Preferably, the *Salvia miltiorrhiza* extract used in the present invention has a minimum Tanshinone IIa content of at least 2.0 percent.

The *Schisandra chinensis* is preferably employed in the form of a pharmaceutical grade extract that can be obtained commercially from, for example, a Chinese manufacturer, the Institute of Medicinal Plant Development, Haiding District, Xibeiwang, Beijing 100094, China. Pharmaceutical grade *Schisandra chinensis* extract manufactured in China is standardized for a Schisandrol A content of no less than 2.0 weight percent. The pharmaceutical grade extract must pass extensive safety and efficacy procedures. Preferably, when employed in the practice of the present invention the *Schisandra chinensis* extract has a Schisandrol A content of from 1.0 to 50 weight percentage. Preferably, the *Schisandra chinensis* extract used in the present invention has a minimum Schisandrol A content of at least 2.0 weight percent.

The species of the present invention each support healthy liver function and in combination may be used to reduce or alleviate the symptoms associated with Hepatitis viral infection, especially Hepatitis C viral infection.

According to a second aspect of the present invention there is provided method of treating a patient to reduce or alleviate the symptoms of Hepatitis, particularly Hepatitis C, or to support healthy liver function comprising administering a botanical drug, or dietary supplement according to the first aspect of the present invention.

According to a third aspect of the invention there is provided the use of a botanical drug or dietary supplement according to the first aspect of the present invention in combination with another drug to reduce or alleviate the symptoms of Hepatitis, particularly Hepatitis C, or to support healthy liver function.

The another drug is preferably interferon and the composition of the invention may be provided simultaneously or sequentially with the interferon.

Thus, the invention also provides a method of treating, reducing or alleviating the symptoms of Hepatitis C in human subjects, which method comprises the administration thereto of a therapeutically effective amount of a botanical drug of the invention. The invention also provides a method of supporting healthy liver function in human subjects, which method comprises the administration thereto of a therapeutically effective amount of botanical drug of the invention.

The herbal composition may also be used to supplement the diet. The invention accordingly provides a method of dietary supplementation which comprises the administration to human subjects of a composition of the invention as described above in an amount effective to support healthy liver function.

The botanical drug or dietary supplement preferably contains each species in an amount, relative to the total weight of all of the botanical raw materials or botanical ingredients, as follows:

(a) *Silybum* spp. from 22-48%;
(b) *Astragalus* spp. or *Hedysarum* spp. from 20-63%;
(c) *Salvia* spp. from 13-48%; and
(d) *Schisandra* spp. from 2-19%.

More preferably still each species is present in an amount as follows:

(a) *Silybum* spp. from 30-40%;
(b) *Astragalus* spp. or *Hedysarum* spp. from 20-30%;
(c) *Salvia* spp. from 20-30%; and
(d) *Schisandra* spp. from 7.5-15%.

According to yet a further aspect of the present invention there is provided a botanical drug or dietary supplement, for the treatment of or for use in patients with Hepatitis C infection, comprising botanical raw materials, botanical drug substances or botanical ingredients from a species of each of the genera:

(a) *Silybum*;
(b) *Astragalus* or *Hedysarum*;
(c) *Salvia*; and
(d) *Schisandra* in an amount by weight relative to the total weight of the botanical raw materials, botanical drug substances or botanical ingredients as follows:

(a) *Silybum* spp. no less than 22% and more preferably no less than 30%;
(b) *Astragalus* spp. or *Hedysarum* spp. no less than 20%
(c) *Salvia* spp. no less than 13% and more preferably no less than 20%; and
(d) *Schisandra* spp. no less than 2% and more preferably no less than 7.5%.

According to the present invention, a therapeutically effective amount of the compositions of the invention are amounts sufficient to reduce or alleviate the symptoms of HCV infection while minimizing harmful side effects. In one embodiment, the therapeutically effective amount is an amount sufficient to reduce or alleviate the symptoms of chronic Hepatitis C without causing harmful side effects. In another embodiment, the therapeutically effective amount is an amount sufficient to normalize or support healthy liver function without causing harmful side effects.

The dosage to be administered will vary and depend on the age, weight, sex and condition of the patient. Typical daily dosages of each of the plant based components (illustrated by way of example only with reference to the preferred species) are as follows (weights refer to a dry botanical raw material equivalent):

| | |
|---|---|
| *Silybum marianum*: | 2–15 g |
| *Astragalus membranaceus* var *mongholicus*: | 9–30 g |
| *Salvia miltiorrhiza*: | 9–15 g |
| *Schisandra chinensis*: | 1.5 g–6 g |

Dosages can be readily determined by one of ordinary skill in the art and can be readily formulated into the present supplemental and pharmaceutical compositions.

Botanical raw materials, botanical drug substances and botanical ingredients can be formulated into a medicament, dietary supplement or nutraceutical by conventional methods.

A nutraceutical is a food ingredient, food supplement or food product which is considered to provide a medical or health benefit, including the prevention and treatment of disease. In general a nutraceutical is specifically adapted to confer a particular health benefit on the consumer. A nutraceutical typically comprises a micronutrient such as a vitamin, mineral, herb or phytochemical at a higher level than would be found in a corresponding regular food product. That level is typically selected to optimise the intended health benefit of the nutraceutical when taken either as a single serving or as part of a diet regimen or course of nutritional therapy.

A botanical drug or dietary supplement of the present invention may be formulated into a medicament or dietary supplement by mixing with a dietetically or pharmaceutically acceptable carrier or excipient. Such a carrier or excipient may be a solvent, dispersion medium, coating, isotonic or absorption delaying agent, sweetener or the like. Suitable carriers may be prepared from a wide range of materials including, but not limited to, diluents, binders and adhesives, lubricants, disintegrants, colouring agents, bulking agents, flavouring agents, sweetening agents and miscellaneous materials such as buffers and adsorbents that may be needed in order to prepare a particular dosage form. The use of such media and agents for pharmaceutically active substances is well known in the art. Except insofar as any conventional media or agent is known to be incompatible with the plant based composition of the present invention, its use in the present compositions is contemplated.

For example, a solid oral forms may contain, together with the active components, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dyestuffs, sweeteners; wetting agents such as lecithin, polysorbates, lauryl sulphates and macrogol (polyethylene glycol). Such preparations may be manufactured in known manners, for example by means of mixing, granulating, tabletting, sugar coating, or film-coating processes.

Liquid dispersions for oral administration may include water solutions, tinctures, syrups, emulsions and suspensions. The syrups may contain as carrier, for example, saccharose or saccharose with glycerol and/or mannitol and/or sorbitol. In particular, a syrup for diabetic patients can contain as carriers only products, for example sorbitol, which do not metabolise to glucose or which only metabolise a very small amount to glucose. The suspensions and the emulsions may contain as carrier, for example, a natural gum, agar, sodium alginate, pectin, methylcellulose, carboxymethylcellulose or polyvinyl alcohol.

The botanical drug or dietary supplement of the present invention is also suitably formulated into granules or a powder. In this form it can be readily dispersed in water or other liquid such as tea or a soft drink for human patients to drink. It may also be encapsulated, tabletted or formulated with a physiologically acceptable vehicle into unit dosage forms. A unit dosage can comprise a therapeutically effective amount of the extract for a single daily administration, or it can be formulated into smaller quantities to provide for multiple doses in a day. The composition may thus, for instance, be formulated into tablets, capsules, syrups, elixers, enteral formulations or any other orally administrable form. Examples of physiologically acceptable carriers include water, oil, emulsions, alcohol or any other suitable material The present invention will be further illustrated, by way of Example, only with reference to the following formulations and data in which:

BEST MODE FOR CARRYING OUT THE INVENTION

EXAMPLE 1

Figure 1:
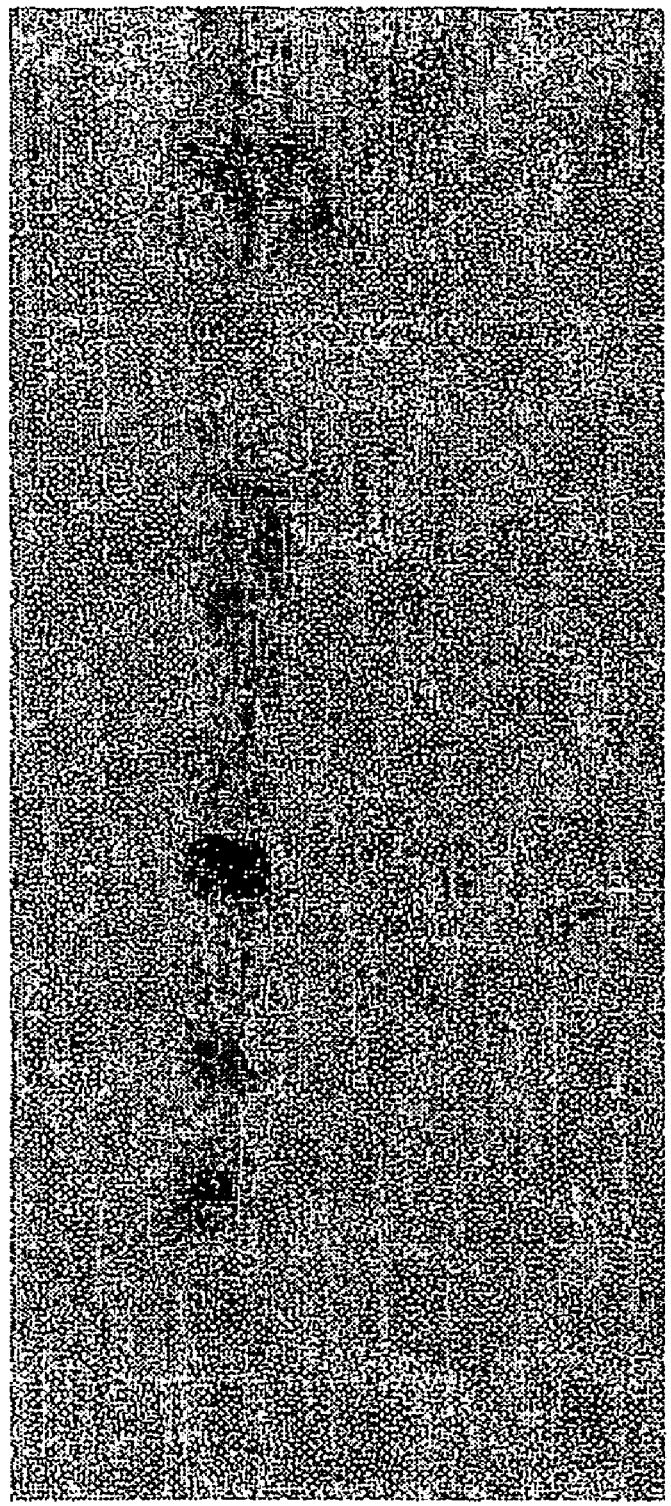
FIG. 1 is a TCL picture of the BDS of *Astragalus membranaceus* var *mongholicus;*

Preparation of Botanical Drug from Botanical Drug Substances

Standardised extracts of *Silybum marianum* (fruit), *Salvia miltiorrhiza* (root), *Schisandra chinensis* (fruit), and *Astragalus membranaceus* var *mongholicus* (root) were made separately using extraction procedures designed specifically for each herb in order to achieve the desired therapeutic potency of the extracts. The extracts were dried and the resulting dry powdered extracts mixed in the proportions shown below (the weights are given both for the extracts and as an equivalent by weight of dry botanical raw material).

(a) *Silybum marianum;* from 0.200 g to 0.250 g (equivalent to 12 g to 15 g of botanical raw material), (b) *Astragalus membranaceus* var *mongholicus;* 0.585 g to 1.95 g (equivalent to 9 g to 30 g of botanical raw material)

(c) *Salvia miltiorrhiza;* 0.225 g to 0.375 g (equivalent to 9 g to 15 g of botanical raw material) and (d) *Schisandra chinensis;* 0.150 g to 0.600 g (equivalent to 1.5 g to 6 g of botanical raw material.

EXAMPLE 2

Formulation Into a Suspension Mixture

The spray-dried botanical drug substances of Example 1 were formulated into a suspension dosage form by mixing the spray-dried botanical drug substances with:

a) one or more gellants or thickeners comprising at least one xanthum gum having a particle size distribution such that 100% by weight of the particles pass a 60 mesh sieve, 95% by weight of the particles pass a 80 mesh sieve and 70% by weight of the particles pass a 200 mesh sieve, b) one or more fillers; and c) one or more wetting agents and or surfactants.

The resulting formulation, referred to as the PYN17 suspension powder mixture, contained the following:

| Composition: | per sachet |
|---|---|
| Active ingredients: | |
| Milk Thistle Fruit dry extract: | 0.200 g |
| Chinese Sage Root dry extract: | 0.225 g |
| *Schisandra* Fruit dry extract: | 0.400 g |
| *Astralagus* Root dry extract: | 0.585 g |
| Excipients: | |
| Macrogol 6000 powder: | 0.600 g |
| Ferwogel 30.385 (molecular weight 3.5–4.0 × $10^6$): | 0.070 g |
| Mannitol EZ: | 0.160 g |
| Aerosil 200: | 0.050 g |
| Aspartame: | 0.050 g |
| Caramel powder: | 0.100 g |
| Peppermint powder aroma: | 0.060 g |

EXAMPLE 3

Activity of PYN17 Suspension Powder Mixture

A sachet of the suspension powder was re-suspended in 2.5 ml water and further diluted 1 in 7. The incompletely dissolved suspension was filtered and the soluble fraction tested.

10 µl of solution was tested in 100 µl culture of cells at a concentration of 1/70. Concentrations of 1/350 and 1/1750 were also used to determine toxicity.

To test toxicity the cells were cultured with Replicon cells for 72 hours, and tritiated thymidine was added 18 hours prior to harvesting.

Results:

Tritiated Thymidine Incorporation.

| Dilution PYN-17 | Well 1 cpm | Well 2 cpm | Well 3 cpm | Well 4 cpm | Well 5 cpm | Mean cpm |
|---|---|---|---|---|---|---|
| 1/70 | 18 | 24 | 65 | 51 | 77 | |
| 1/350 | 41010 | 32432 | 34719 | 30311 | 32371 | 34169 |
| 1/1750 | 36210 | 28315 | 32424 | 38230 | 39815 | 34999 |
| 0 | 31609 | 35373 | 36199 | 36281 | 36210 | 35134 |

Inhibition of Replication Measured by Expression of Renilla Luciferase.

The 1/70 dilution was toxic to the cells (as under the microscope the cells were dead). This dilution was not used in the Replicon assay and a further lower dilution was used.

| Dilution PYN17 | Well 1 luciferase activity | Well 2 | Well 3 | Well 4 | Well 5 | Mean luciferase activity | +/− SD |
|---|---|---|---|---|---|---|---|
| 1/350 | 531292 | 234958 | 614669 | 479425 | 725350 | 517139 | 183108 |
| 1/1750 | 594920 | 972891 | 889324 | 595922 | — | 763264 | 196789 |
| 1/8750 | 880338 | 1005370 | 608077 | 644105 | 806756 | 788929 | 165228 |
| 0 | 1139829 | 870757 | 820645 | 724027 | — | 888815 | 178079 |

CONCLUSION

At a 1/350 dilution an inhibition of 41.8% was noted indicating activity against Hepatitis C virus.

The results may be slightly skewed by one very low result (well 2).

The control (no suspension powder) may also be skewed by the one high result (well 1).

At 1/350 the mean without the low result was 587684

The control without the high result (well 1) was 805143

Excluding the single high and low results the % inhibition was 27%.

EXAMPLES 4-7

These illustrate the extraction methods used in the preparation of the botanical drug substances used in the botanical drug of the invention.

EXAMPLE 4

Preparation of a Botanical Drug Substance from a *Silybum* spp.

Figure 10:
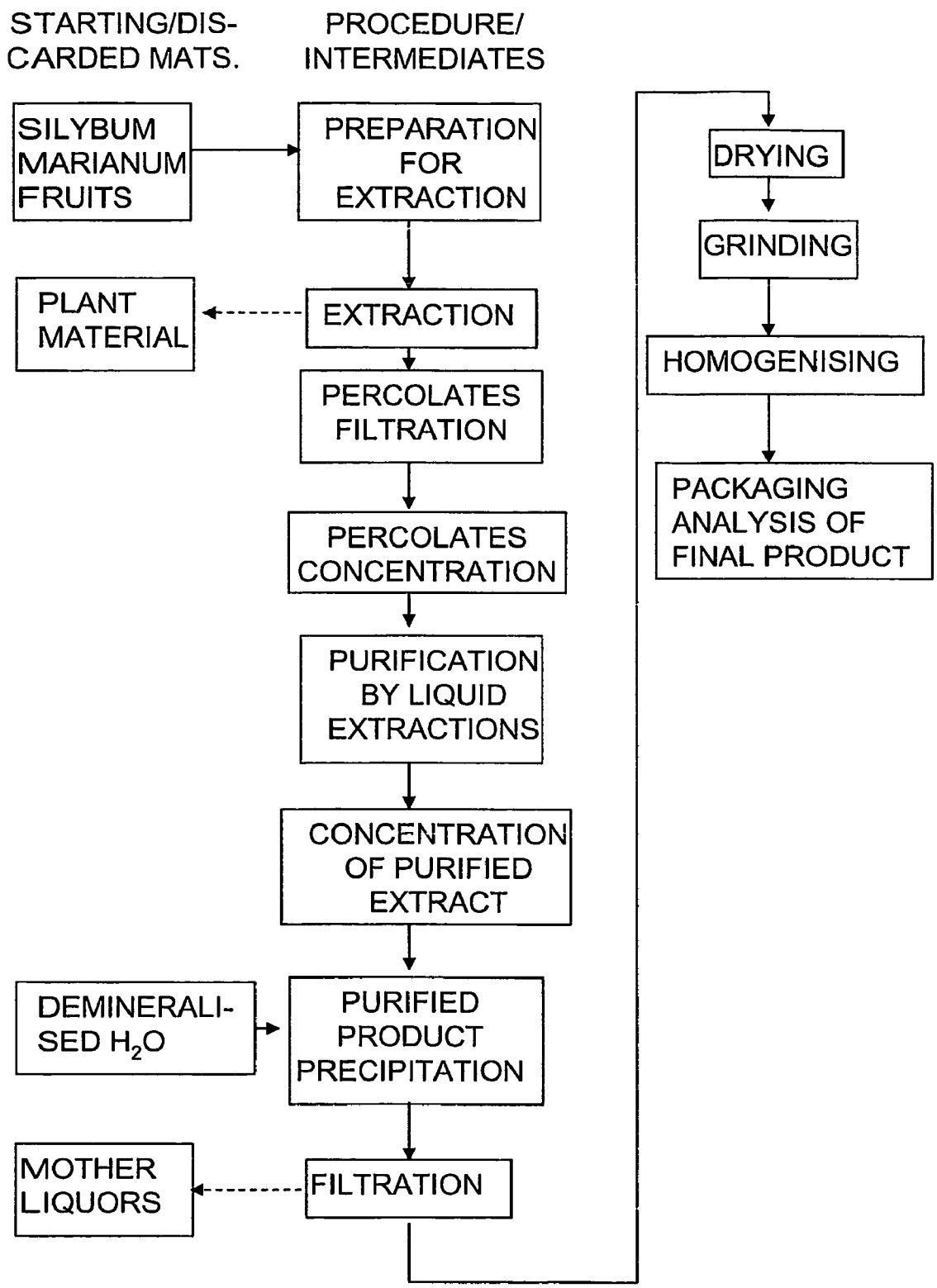
FIG. 10 is a flow chart showing the manufacture process for producing a botanical drug substance from *Silybum* spp.

Referring to FIG. 10 there is illustrated a process for producing a botanical drug substance of a *Silybum* spp. The fruits are prepared for extraction, undergo an extraction, the resulting solution is filtered, and concentrated. The concentrated purified extract then undergoes a further clean up process in which purified product is precipitated, filtered and the filtrate dried and ground for packing. Such a product can be obtained from Indena SpA.

EXAMPLE 5

Preparation of a Botanical Drug Substance from a *Astragalus* spp.

Figure 11:
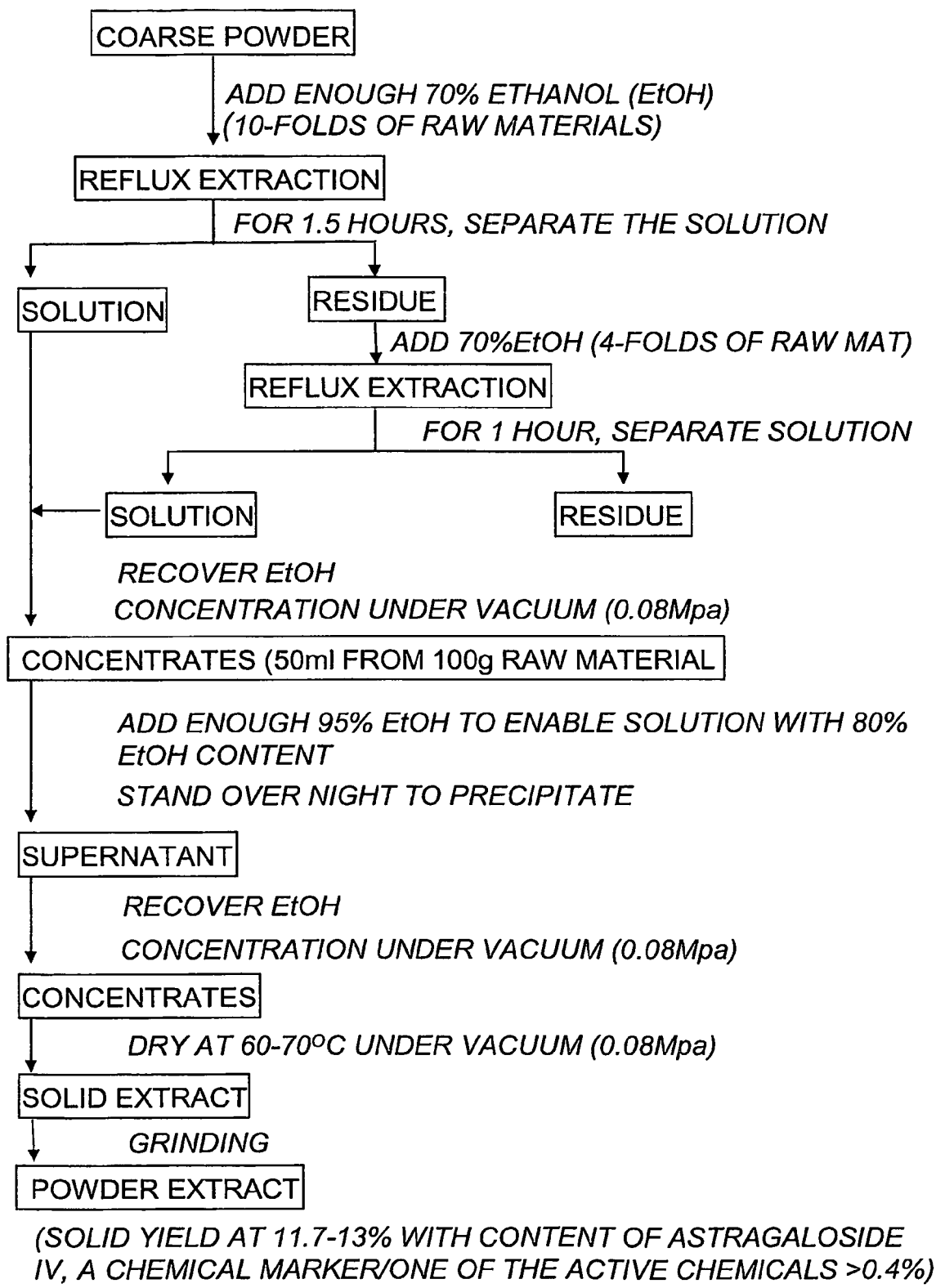
FIG. 11 is a flow chart showing the manufacture process for producing a botanical drug substance from *Astragalus* spp.

(The preparation of a botanical drug substance from a *Hedysarum* spp. is equivalent) Referring to FIG. 11 *Astragalus* spp. root material is dried in an oven at 60° C. for 3 hours, pulverised into a coarse powder, passed through a sieve (10 mesh) and subjected to extraction as per the flow chart. The extraction process is an ethanolic extraction. The concentrate obtained is re-dissolved in ethanol, any precipitate removed and the product concentrated and dried. The method yields a solid content in excess of 10% with an Astragaloside content of greater than 0.4%.

EXAMPLE 6

Preparation of a Botanical Drug Substance from a *Salvia* spp.

Figure 12:
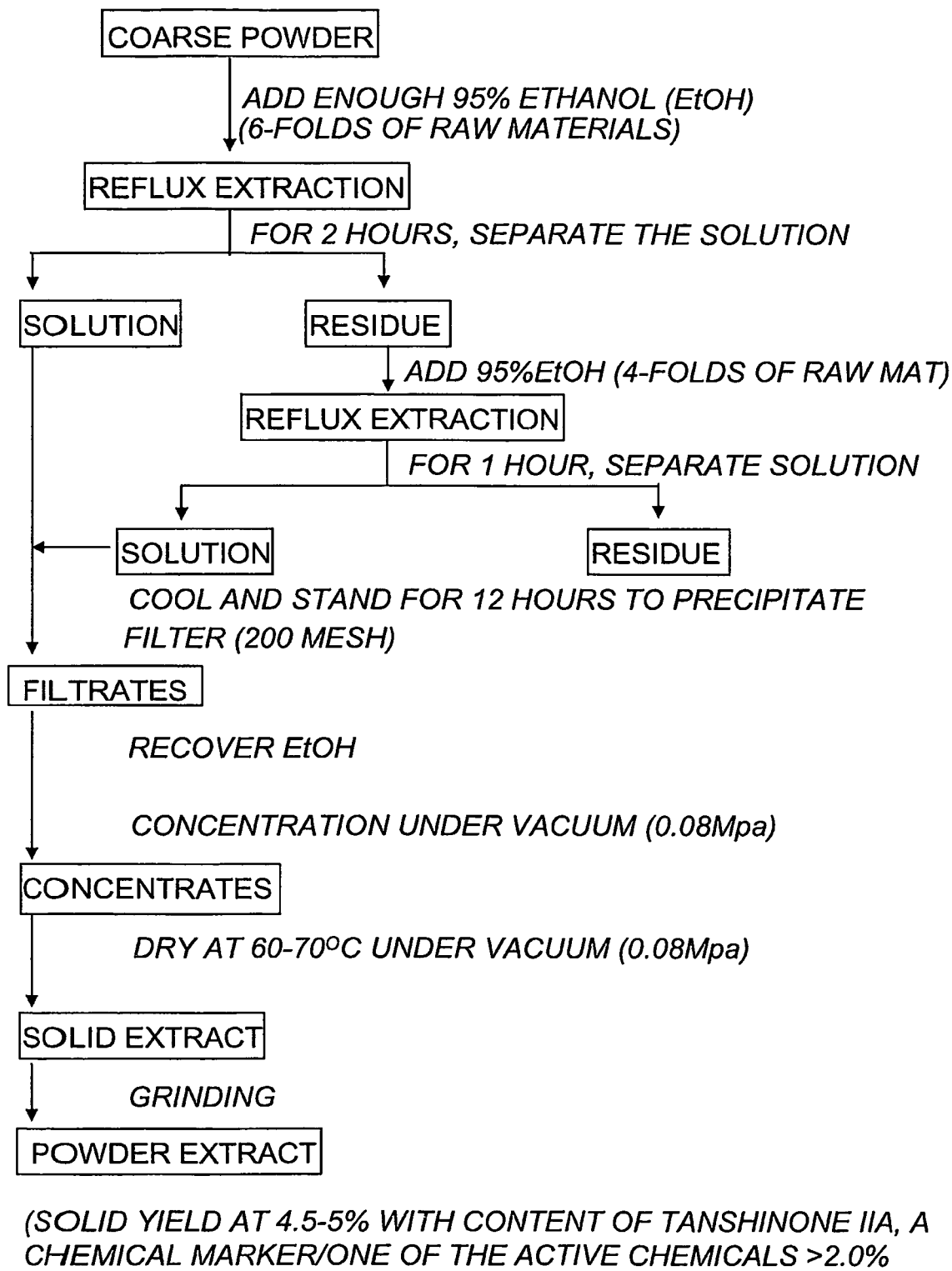
FIG. 12 is a flow chart showing the manufacture process for producing a botanical drug substance from *Salvia* spp.

Referring to FIG. 12 the *Salvia* spp. root material is dried in an oven at 60° C. for 3 hours, pulverised into a coarse powder, passed through a sieve (10 mesh) and subjected to extraction as per the flow chart. The extraction process is an ethanolic extraction and the resulting concentrate is dried. The method yields a solid content in excess of 4% with a Tanshinone IIA content of greater than 1.5%.

EXAMPLE 7

Preparation of a Botanical Drug Substance from a *Schisandra* spp.

Figure 13:
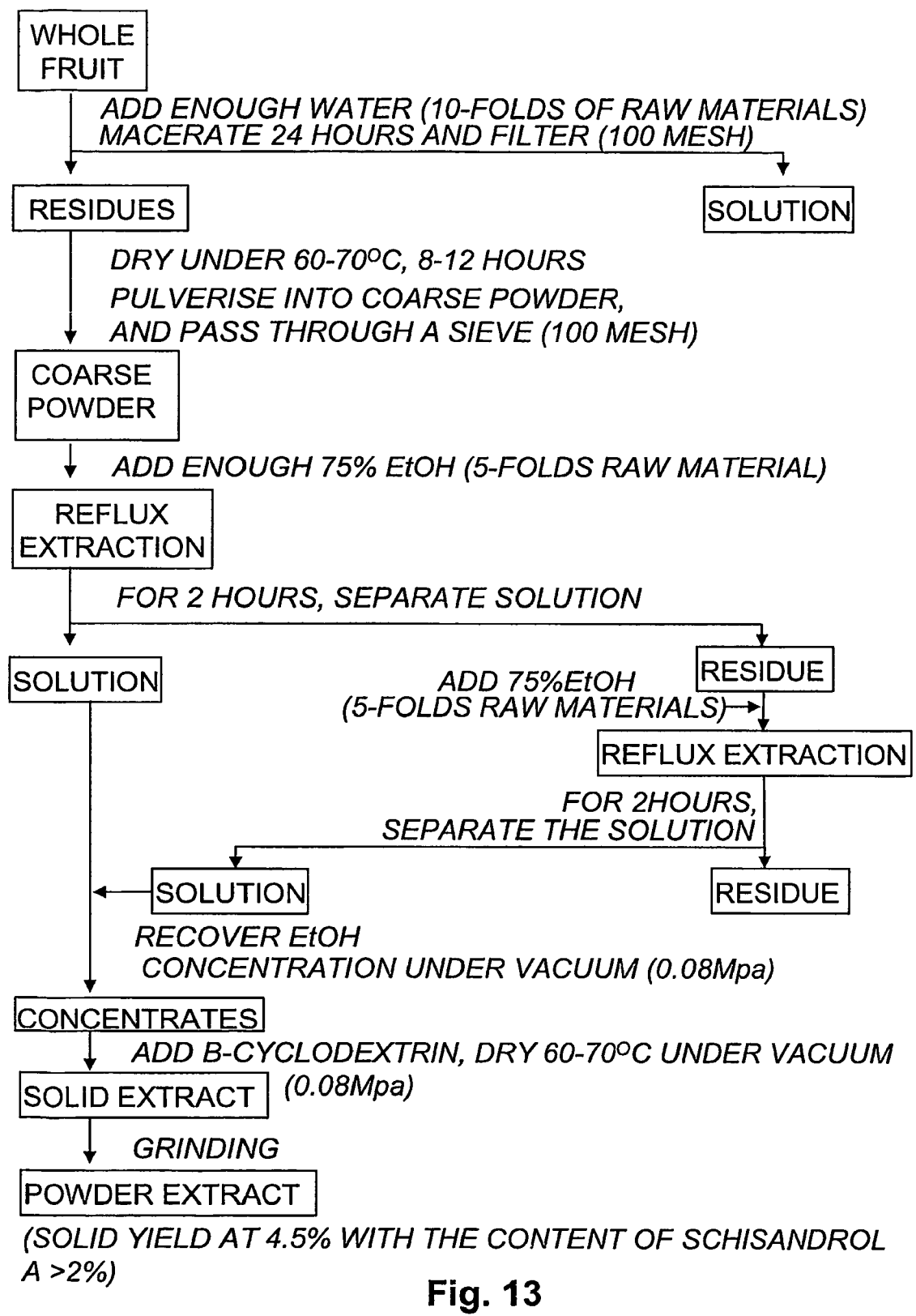
FIG. 13 is a flow chart showing the manufacture process for producing a botanical drug substance from *Schisandra* spp.

Referring to FIG. 13 the *Salvia* spp. fruit is macerated in water and filtered. The filtrate residues are dried, powdered and subjected to an ethanolic extraction, and the resulting concentrate is dried. The method yields a solid content in excess of 4% with a Schisandrol A content of greater than 2%.

EXAMPLES 8-11

A botanical drug substance obtained from the sources identified, and by the methods described was subject to analysis and the results are given below:

EXAMPLE 8

The botanical drug substance from a *Silybum* spp. was shown by analysis to have the following characteristics

| DETERMINATION | RESULTS | SPECIFICATIONS | U.M |
|---|---|---|---|
| SPECTROPHOTOMETRIC CONTENTS of silymarin, calculated as silybin, according to DAB10 | 70.9 | >=65.0 | % |
| HPLC CONTENTS As sum of silybin and isosilybin | 38.8 | >=30.0 | % |
| CHARACTERS Brownish yellow powder | Complies | Complies | |
| SOLUBLE SUBSTANCES in pantane | 0.25 | <=0.5 | % |
| HPLC: IDENTIFICATION LOSS ON DRYING | Complies | Complies | |
| (T = 80° C., in vacuum t = 3h | 0.0 | <=5.0 | % |
| SULPHATED ASH According to Ph. Eur. | 0.33 | <=1.0 | % |
| HEAVY METALS According to Ph. Eur. Method A | Complies | <=100 | ppm |
| RESIDUAL ORGANIC SOLVENTS | | | |
| Ethanol | 0.4 | <=1.0 | % |
| Ethyl Acetate | <0.0008 | <=0.01 | % |
| Hexane | Complies | <=0.01 | % |
| MICRBIOLOGICAL CONTROL According to Ph. Eur. | | | |
| BACTERIA Maximum limit of acceptance: 5 × 1000 cfu/g TM/0113 | <1000.0 | <=1000.0 | cfu/g |
| FUNGI Maximum limit of acceptance: 5 × 100 cfu/g TM/0118 | <100.0 | <=100.0 | cfu/g |
| ENTEROBACTERIA TM/0015 and TM/0075 | <100.0 | <=100.0 | cfu/g |
| *STAPHYLOCOCCUS AUREUS. SALMONELLA* TM/0008, TM/0009, TM/0017 and TM/0075 | Absent | Absent | |
| *ESCHERICHIA COLI, PSEUDOMONAS AERUGINOSA* TM/0010, TM0011, TM0016 and TM/0075 | Absent | Absent | |

EXAMPLE 9

The botanical drug substance from the *Astragalus* spp. was shown by analysis to have the following characteristics:

A) Certificate of Analysis

Product Name: *Astragalus* Root Extract (*Astragalus membranaceus* var *mongholicus*)

Batch Number: AMR-200201PE

| TESTS | SPECIFICATION | RESULT |
|---|---|---|
| Appearance | Pale yellow colour | Pass |
| Loss on Drying: | <5% (CP) | 2.65% |
| Particle Size: | 80 mesh | Pass |
| Total Ash | <5.0% | 0.14% |
| Heavy Metals: Lead | <5 ppm | 0.55 |
| Mercury | <1 ppm | 0.84 |
| Arsenic | <1 ppm | 0.61 |
| Cadmium | <0.5 ppm | 0.21 |
| Acid Insoluble Ash | <2.0% | 0.026% |
| Microbial Total viable aerobic count: | <10$^3$ cfu/g | 80 |
| Fungal & Yeast: | <10$^2$ cfu/g | 10 |
| *Escherichia coli*: | Absent in 10 g | Absent |
| *Salmonella* spp.: | Absent in 10 g | Absent |
| Content Assay: | Astragaloside IV > 0.4% | 0.44% |

B) Chemical Analysis

Name of the Product: *Astragalus* Root Extract (*Astragalus membranaceus* var *mongholicus*)

Batch Number: AMR-200201PE

Chemical Analysis:

i) TLC Fingerprint: See FIG. 1 which is a TLC picture of the BDS of *Astragalus membranaceus* var *mongholicus*. The left is the BDS sample and the right the standard reference chemical Astragaloside IV Preparation of Test Solutions:

Add 40 ml of methanol to 1 g of powder extract, shake well and filter. Apply the filtrates to a prepared neutral aluminium oxide column, then follow the method described in Chinese Pharmacopoeia (English Edition, 2000), Page 161, Identification (2), Reference solution: Dissolve chemical reference standard (CRS) Astragaloside IV in methanol to produce a 1 mg/ 1 ml reference solution.

Loadings: Load 2 μl of the test solution and 2 μl of the reference solution, respectively, on foil-backed Silica gel $F_{254}$ plate Merck).

Developing solvent system: chloroform:methanol:water (13:7:2) (Lower layer)

Developing: Add mixed developing solution to a TLC tank and stand for 15 Minute for equilibrium. Put the TLC plate in and develop for 7.5 cm.

Detection:

When sprayed with 10% of sulphuric acid in ethanol and heated at 105° C. a brown spot is obtained in TLC chromatogram of the test solution corresponds in position and colour to the spot of the reference solution. Observe the developed TLC plate under UV365$_{nm}$ light, both reference chemical Astragaloside IV and test solution showed a orange yellow spot at Rf 0.49, ii) HPLC Analysis Equipment: Waters HPLC System, LC 600 pump and UV detector (Model 486).
  Column: Spherisorb S100Ds1, 25 cm×4.6 mm
  Column temperature: 25° C.
  Flow rate: 1.0 ml/min
  Detection wavelength: UV200$_{nm}$
  Mobile phase: acetonitrile:water (1:2)
  Preparation of CRS solution: Dissolve 2 mg of Astragaloside IV in mobile phase solution in a 10 ml volumetric flask.

Preparation of Test Solutions:

Weigh accurately 1.0 g of powder extract, add 50 ml of 2% KOH in methanol, heat and reflux on water bath for 1 hour and filter. Repeat the procedure for three times. Combine the filtrates and recover the solvent. Add 25 ml of water to dissolve the residue, wash with 50 ml of ether. To the aqueous solution, extract with 25 ml of n-butanol (saturated in water) for three times. Combine butanol solution, wash twice with 25 ml of water, respectively, then wash with 25 ml of potassium dihydrogen phosphate, recover the solvent. Add accurately 10 ml of mobile phase solution to the residue shake well, filter through milipore (0.45 μm) as test solution.

Quantity of injection: Inject 20 μl of CRS solution and 20 μl of test solution, respectively.

Figure 4:
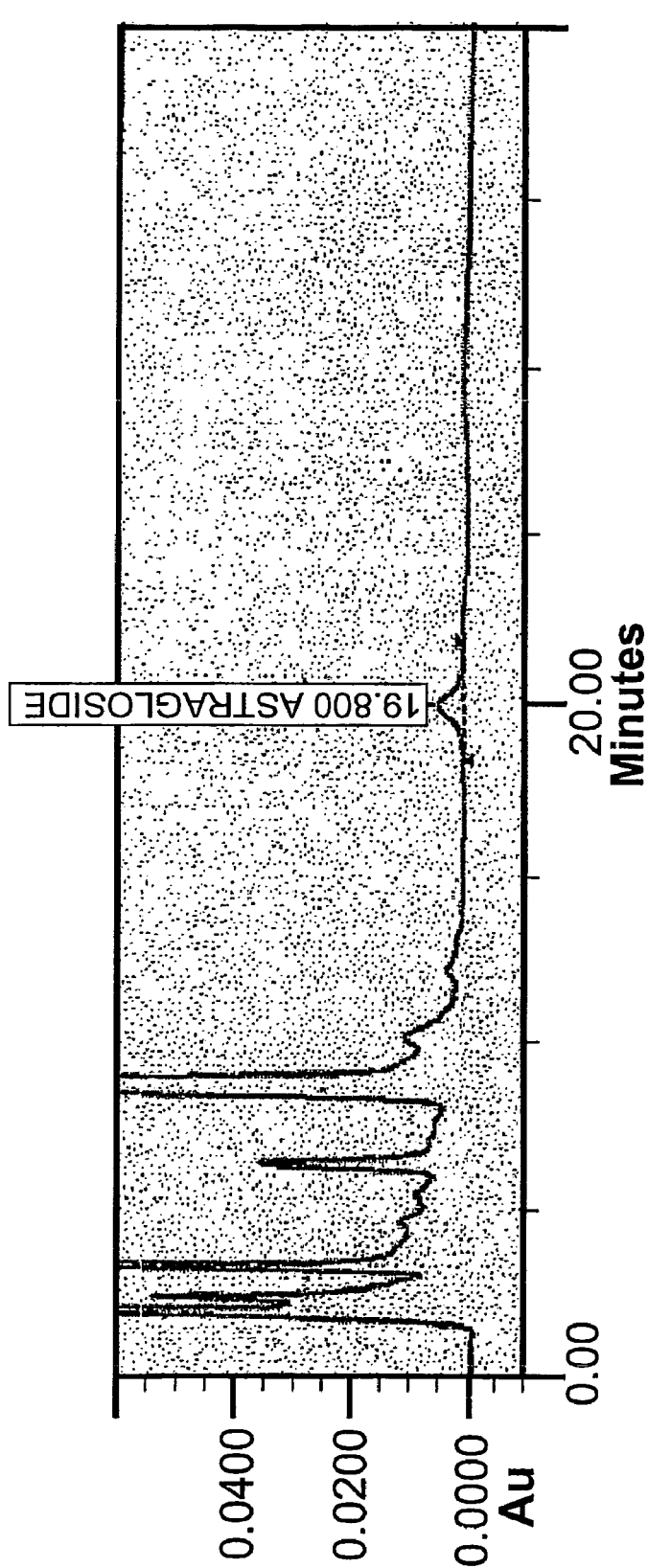
FIG. 4 is a HPLC chromatogram of the BDS of *Astragalus membranaceus;*
Figure 5:
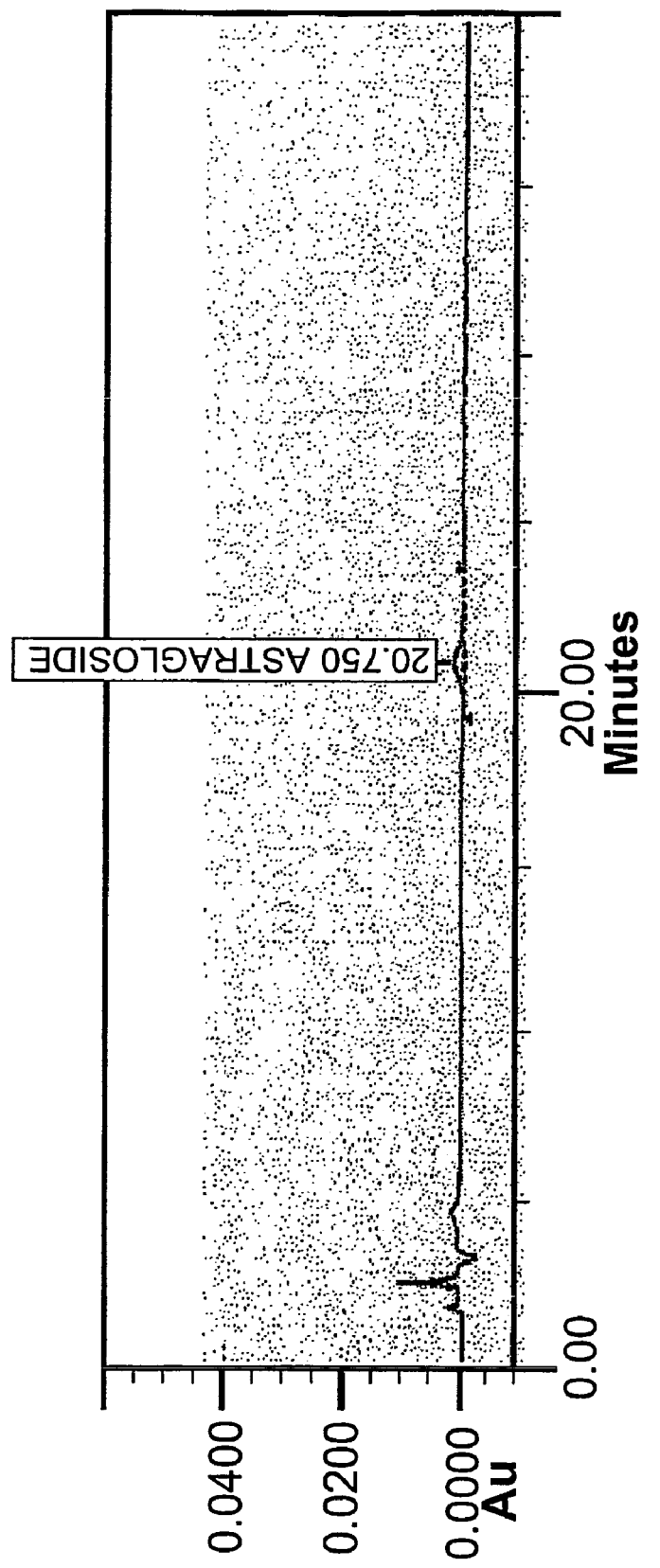
FIG. 5 is a HPLC chromatogram of Astragaloside (a marker of *Astragalus membranaceus* var *mongholicus*)

Result: See chromatograms in FIGS. 4 and 5. FIG. 4 (the BDS) shows at least 10 clearly identifiable peaks including Astragaloside IV at a retention time of about 20 minutes. The area under the graph indicates a presence of at least 0.4% by weight of Astragaloside IV. The FIG. 5 chromatogram is a control with the marker alone.

| Specifications for Astragaloside IV content (% w/w) | Result (% w/w) |
| --- | --- |
| >0.4 | 0.44 |

EXAMPLE 10

The botanical drug substance from the *Salvia* spp. was shown by analysis to have the following characteristics:

A) Certificate of Analysis

Product Name: *Salvia Miltiorrhiza* Root Extract (*salvia miltiorrhiza*)
Batch Number: SMR-200201PE

| TESTS | SPECIFICATION | RESULT |
| --- | --- | --- |
| Appearance | Dark red colour | Pass |
| Loss on Drying: | <5% (CP) | 3.24% |
| Particle Size: | 80 mesh | Pass |
| Total Ash | <5.0% | 0.38% |
| Acid Insoluble Ash | <2.0% | 0.04% |
| Heavy Metals: Lead | <5 ppm | 0.65 |
| Mercury | <1 ppm | 0.14 |
| Arsenic | <1 ppm | 0.62 |
| Cadmium | <0.5 ppm | 0.38 |
| Microbial Total viable aerobic count: | <10$^3$ cfu/g | 100 |
| Fungal & Yeast: | <10$^2$ cfu/g | 20 |
| *Escherichia coli*: | Absent in 10 g | Absent |
| *Salmonella* spp.: | Absent in 10 g | Absent |
| Content Assay: | Tanshinone$_A$ > 1.5% | 1.98% |

B) Chemical Analysis

Name of the Product: *Salvia Miltiorrhiza* Root Extract (*Salvia miltiorrhiza*)
Batch Number: SMR-200201PE Chemical Analysis:

i) TLC Fingerprints: See FIG. 2 which is a TLC picture of the BDS of *Salvia miltiorrhiza* The left is the BDS sample and the right the standard reference chemical Tanshinone IIA Preparation of Test solutions: Add 1 ml of ethyl acetate to 100 mg of powder extract.

Reference solution: Dissolve chemical reference standard (CRS) Tanshinone II$_A$ in ethyl acetate to produce a 2 mg/1 ml reference solution.

Loadings: Load 5 μl of the test solution and 5 μl of the reference solution, respectively, on foil-backed Silica gel plate (Merck).

Developing solvent system: benzene:ethyl acetate (19:1)

Developing: Add mixed developing solution to a TLC tank and stand for 15 Minute for equilibrium. Put the TLC plate in and develop for 7.5 cm.

Detection: Dry the developed plate in air, a dark red spot obtained in TLC chromatogram of the test solution corresponds in position and colour to the spot of the reference solution at Rf 0.46.

ii) HPLC Analysis

Equipment: Waters HPLC System, LC 600 pump and UV detector (Model 486).
  Column: Spherisorb S100Ds1, 25 cm×4.6 mm
  Column temperature: 25° C.
  Flow rate: 1.0 ml/min
  Detection wavelength: UV270$_{nm}$
  Mobile phase: Methanol: Water (15:5)
  Preparation of CRS solution: Weight accurately 10 mg of Tanshinone IIA to a 50 ml amber volumetric flask and dissolve with methanol to the volume. Accurately measure 2 ml to a 25 ml amber volumetric flask and add methanol to the volume.

Preparation of test solutions: Weigh accurately 30 mg of powder extract to a 25 ml volumetric flask, add 18 ml of methanol and treat under ultrasonic for 5 minutes, then add methanol to the volume.

Quantity of injection: Inject 5 μl of CRS solution and 5 μl of test solution, respectively.

Figure 6:
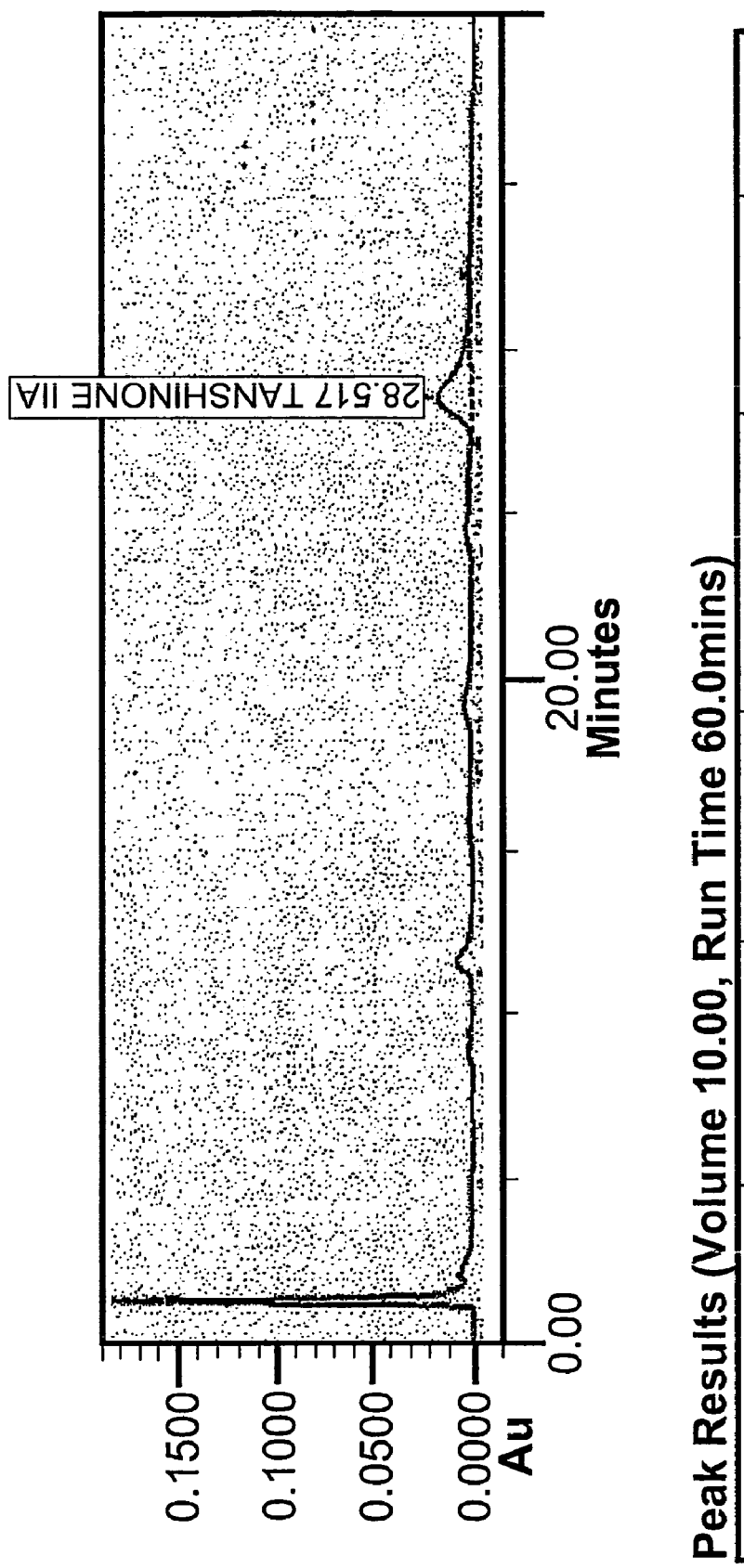
FIG. 6 is a HPLC chromatogram of the BDS of *Salvia miltiorrhiza;*
Figure 7:
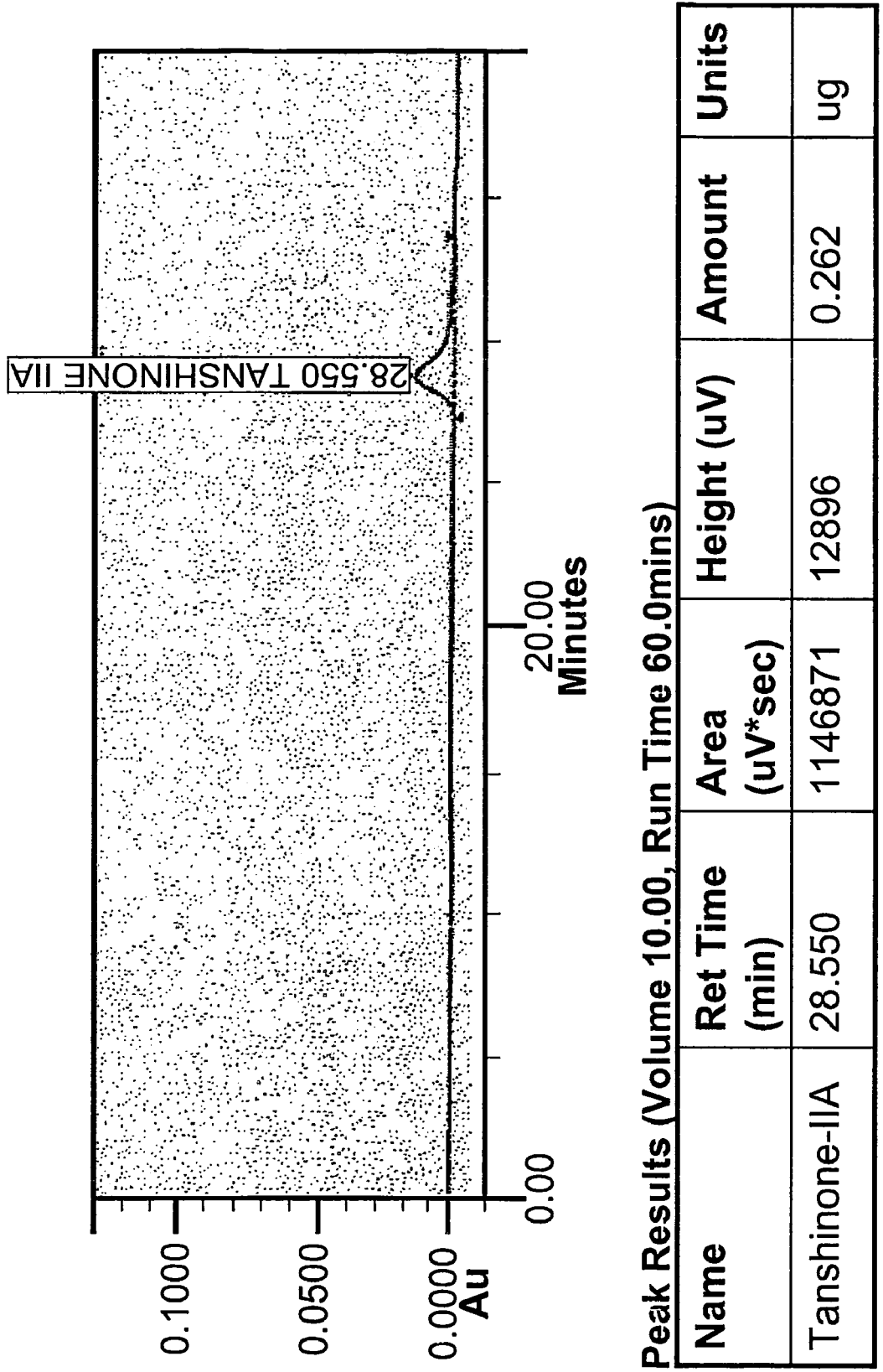
FIG. 7 is a HPLC chromatogram of Tanoshone-IIA (a marker of *Salvia miltiorrhiza*)

Result: See chromatograms in FIGS. 6 and 7. FIG. 6 (the BDS) shows at least 6 identifiable peaks including Tanshinone IIA at a retention time of about 28/29 minutes. The area under the graph indicates a presence of at least 1.5% by weight of Tanshinone IIA. The FIG. 7 chromatogram is a control with the marker alone.

| Specifications for Tanshinone II$_A$ content (% w/w) | Result (% w/w) |
| --- | --- |
| >1.5 | 1.98 |

EXAMPLE 11

The botanical drug substance from the *Schisandra* spp. was shown by analysis to have the following characteristics:

A) Certificate of Analysis

Product Name: *Schisandra* Fruit Extract (*Schisandra chinensis*)

Batch Number: SCF-200201PE

| TESTS | SPECIFICATION | RESULT |
|---|---|---|
| Appearance | Brownish red colour | Pass |
| Loss on Drying: | <5% (CP) | 4.5% |
| Particle Size: | 80 mesh | Pass |
| Total Ash | <5.0% | 0.25% |
| Acid Insoluble Ash | <2.0% | 0.06% |
| Heavy Metals: Lead | <5 ppm | 0.45 |
| Mercury | <1 ppm | 0.47 |
| Arsenic | <1 ppm | 0.74 |
| Cadmium | <0.5 ppm | 0.36 |
| Microbial Total viable aerobic count: | $<10^3$ cfu/g | 90 |
| Fungal & Yeast: | $<10^2$ cfu/g | 10 |
| *Escherichia coli*: | Absent in 10 g | Absent |
| *Salmonella* spp.: | Absent in 10 g | Absent |
| Content Assay | Schizandrol A > 2.0% | 2.4% |

B) Chemical Analysis

Name of the Product: *Schisandra* Fruit Extract (*Schisandra chinensis*)

Batch Number: SCF-200201PE

Chemical Analysis:

i) TLC Fingerprints: See FIG. 3 which is a TLC picture of the BDS of *Schisandra chinensis*. The left is the BDS sample and the right the standard reference chemical Schisandrin A Preparation of Test Solutions:

Add 20 ml of chloroform to 0.5 g of powder extract, ultrasonicate for 10 minutes and filter. Evaporate the filtrates to dryness and dissolve the residue in 1 ml of chloroform as test solution.

Reference solution: Dissolve chemical reference standard (CRS) Schizandrol A in chloroform to produce a 1 mg/1 ml reference solution.

Loadings: Load 2 µl of the test solution and 2 µl of the reference solution, respectively, on foil-backed Silica gel $F_{254}$ plate (Merck).

Developing solvent system: Petroleum ether (30-60° C.): ethyl formate:formic Acid (15:5:1) (upper layer)

Developing: Add mixed developing solution to a TLC tank and stand for 15 minute for equilibrium. Put the TLC plate in and develop for 7.5 cm.

Detection: Dry the developed plate in air, observe the plate under UV 254 nm, a dark spot obtained in TLC chromatogram of the test solution corresponds in position and colour to the spot of the reference solution at Rf 0.14.

ii) HPLC Analysis

Equipment: Waters HPLC System, LC 600 pump and UV detector (Model 2487).

Column: Spherisorb S100Ds1, 25 cm×4.6 mm

Column temperature: 25° C.

Flow rate: 11.0 ml/min

Detection wavelength: $UV250_{nm}$

Mobile phase: Methanol:Water (13:7)

Preparation of CRS solution: Weight accurately 15 mg of Schizandrol A to a 50 ml volumetric flask and dissolve with methanol to the volume to produce a solution with 0.3 mg Schizandrol A/per ml.

Preparation of test solutions: Place 0.25 g of raw material powder (Trough No. 3 sieve) into a volumetric flask, add 18 ml of methanol and ultrasonicate (power 250 w, frequency 20 kHz) for 20 minutes. Add methanol to the volume, mix well and filter.

Quantity of injection: Inject 10 µl of CRS solution and 10 µl of test solution, respectively.

Figure 8:
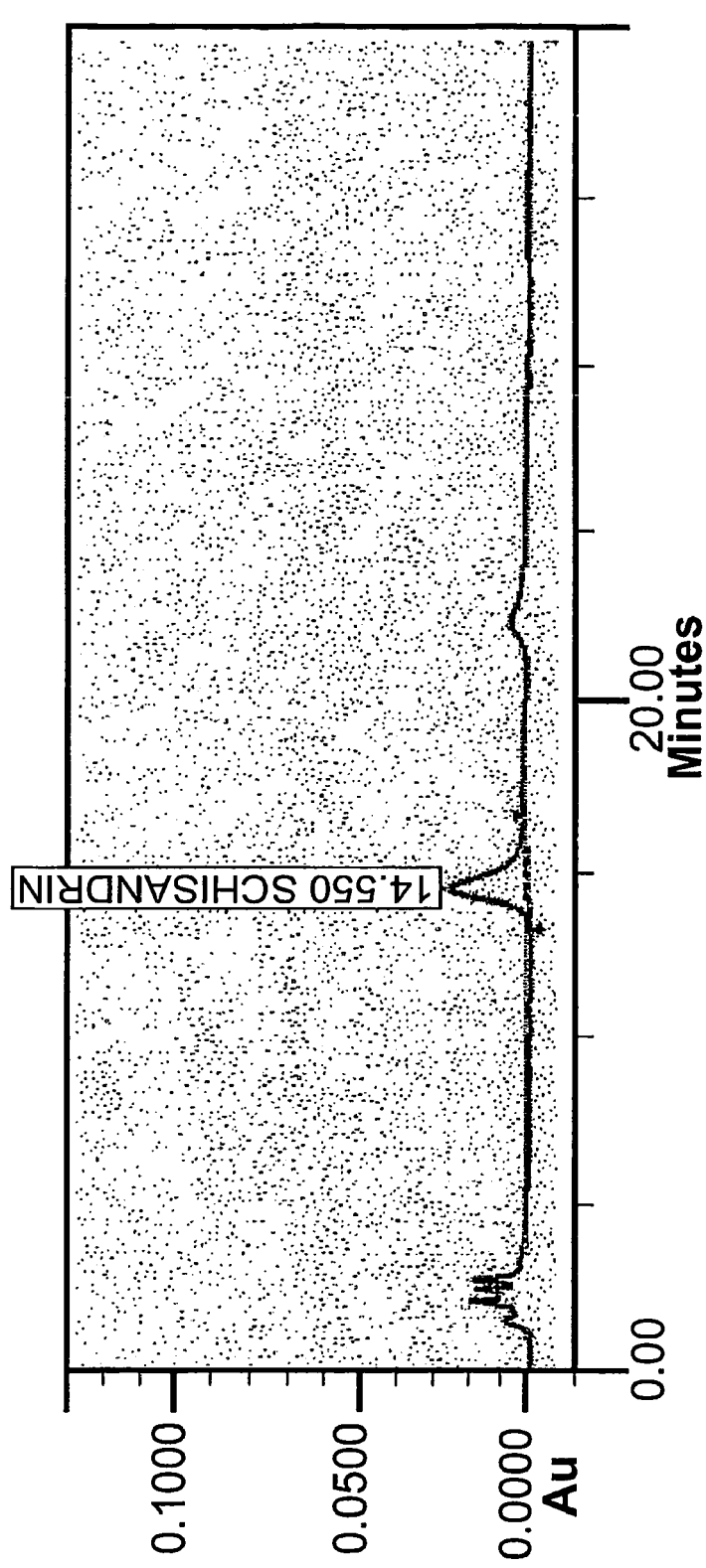
FIG. 8 is a HPLC chromatogram of the BDS of *Schisandra chinensis;*
Figure 9:
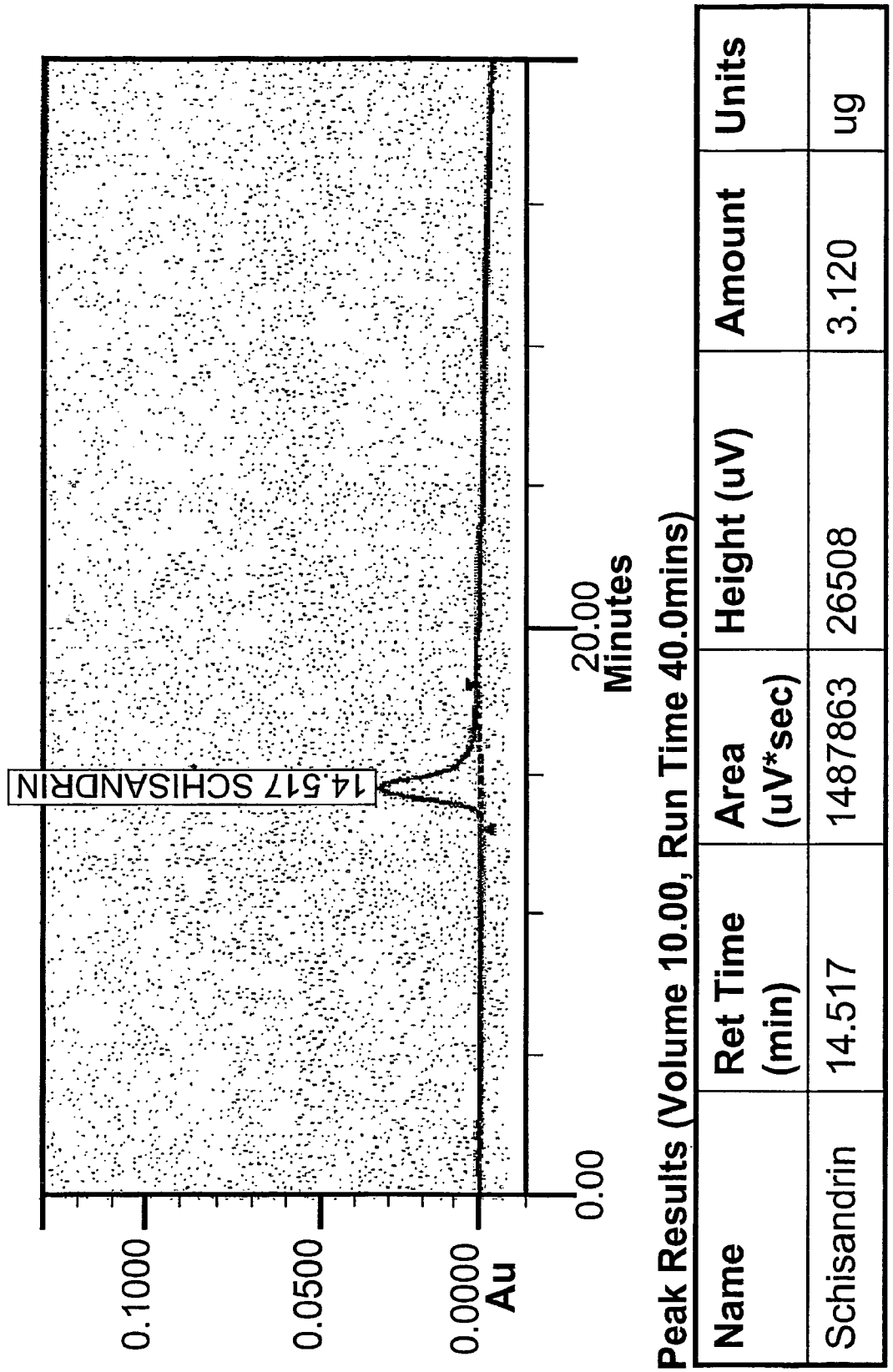
FIG. 9 is a HPLC chromatogram of Schisandrin (a marker of *Schisandra chinensis*)

Result: See chromatograms in FIGS. 8 and 9. FIG. 8 (the BDS) shows at least 6 identifiable peaks including Schizandrol A at a retention time of about 14/15 minutes. The area under the graph indicates a presence of at least 2% by weight of Schizandrol A. The FIG. 9 chromatogram is a control with the marker alone.

| Specifications for Schizandrol A content (% w/w) | Result (% w/w) |
|---|---|
| >2.0 | 2.4 |

The invention claimed is:

1. A botanical drug or dietary supplement, for the treatment of Hepatitis C infection, consisting essentially of effective amounts of extracts from the following plant species sources:
   (a) the fruit of *Silybum marianum*;
   (b) the root of *Astragalus membranaceus* var *mongholicus* or *Hedysarum polybotrys*;
   (c) the root of *Salvia miltiorrhiza, Salvia bowleyana* or *Salvia przewalskii*; and
   (d) the fruit of *Schisandra chinensis* or *Schisandra sphenanthera*.

2. A botanical drug or dietary supplement as claimed in claim 1 wherein each species is present in an amount, relative to the total weight of all extracts, as follows:
   (a) *Silybum* from 22-48%;
   (b) *Astragalus* or *Hedysarum* spp. from 20-63%;
   (c) *Salvia* from 13-48%; and
   (d) *Schisandra* from 2-19%.

3. A botanical drug or dietary supplement as claimed in claim 2 wherein each extract is present in an amount by weight percent as follows:
   (a) *Silybum* from 30-40%;
   (b) *Astragalus* or *Hedysarum* from 20-30%;
   (c) *Salvia* from 20-30%; and
   (d) *Schisandra* from 7.5-15%.

4. A botanical drug or dietary supplement as claimed in claim 3 wherein each extract is present in an amount by weight percent as follows:
   (a) *Silybum* about 35%;
   (b) *Astragalus* or *Hedysarum* about 26%;
   (c) *Salvia* about 26%; and
   (d) *Schisandra* about 11%.

5. A botanical drug or dietary supplement as claimed in claim 1 further including excipients.

6. A botanical drug or dietary supplement as claimed in claim 1 wherein the extract from *Silybum* is standardized against a marker of silybin.

7. A botanical drug or dietary supplement as claimed in claim 1 wherein the extract from *Silybum* comprises at least 30% by weight silybin and isosilybin when calculated using HPLC.

8. A botanical drug or dietary supplement as claimed in claim 6 wherein the standardized extract of *Silybum* is a brownish yellow powder which has:
   (i) no less than 30% silybin by HPLC;
   (ii) no more than 0.5% soluble in pentane;
   (iii) a sulphated ash content of no more than 1% by weight;
   (iv) a heavy metal content of no more than 100 ppm;
   (v) a residual organic solvent content of no more than 1% ethanol, no more than 0.01% ethyl acetate and no more than 0.01% hexane by weight;
   (vi) a bacterial content of no more than 1000 cfu/g; and
   (vii) a fungal content of no more than 100 cfu/g.

9. A botanical drug or dietary supplement as claimed in claim 1 wherein the extract from *Astragalus* is standardized against a marker of Astragaloside IV.

10. A botanical drug or dietary supplement as claimed in claim 9 wherein the extract from *Astragalus* comprises at least 0.4% by weight Astragaloside IV when calculated using HPLC.

11. A botanical drug or dietary supplement as claimed in claim 9 wherein the extract from *Astragalus* has a TLC chromatographic fingerprint substantially as illustrated in FIG. 1 or a HPLC fingerprint substantially as illustrated in FIG. 4.

12. A botanical drug or dietary supplement as claimed in claim 9 wherein the standardized extract of *Astragalus* is a pale yellow powder which has:
   (i) no less than 0.4% Astragaloside IV by weight;
   (ii) a total ash content of no more than 5% by weight;
   (iii) an acid insoluble ash content of no more than 2% by weight; and
   (iv) a microbial total viable aerobic count of no more than of 1000 cfu/g.

13. A botanical drug or dietary supplement as claimed in claim 1 wherein the extract from the *Salvia* is standardized against a marker of Tanshinone II A.

14. A botanical drug or dietary supplement as claimed in claim 13 wherein the extract from the *Salvia* comprises at least 1.5% by weight of Tanshinone IIA as calculated using HPLC.

Figure 2:
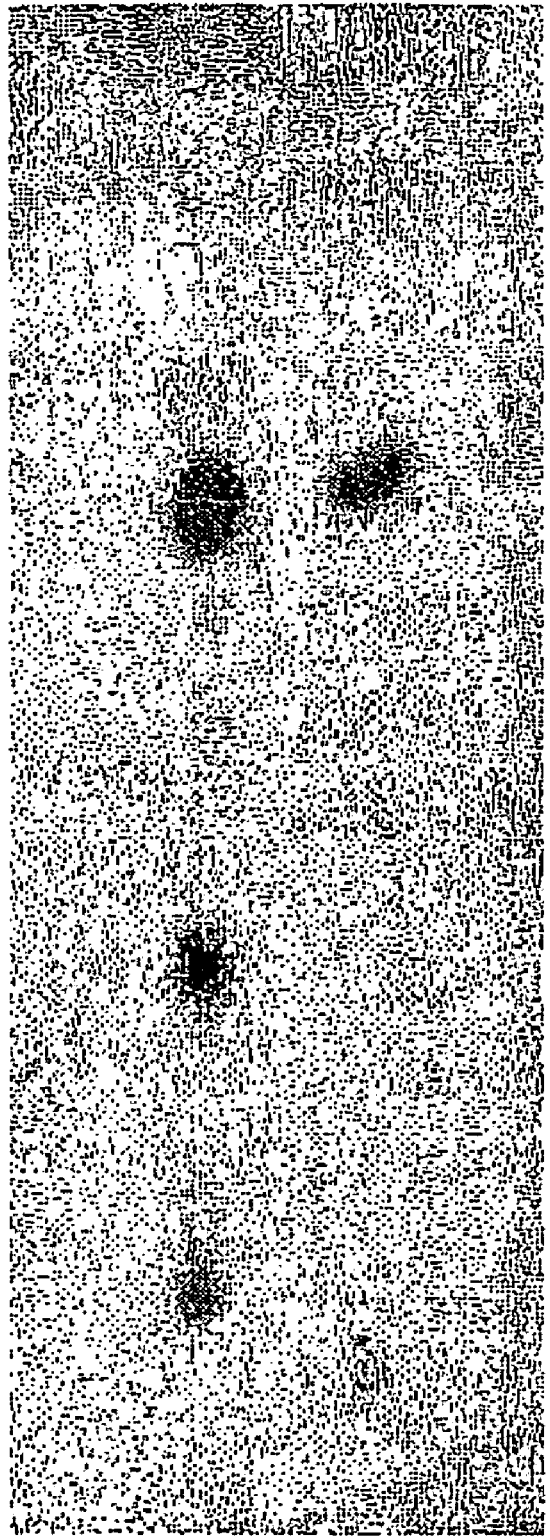
FIG. 2 is a TCL picture of the BDS of *Salvia miltiorrhiza;*

15. A botanical drug or dietary supplement as claimed in claim 13 wherein the extract from the *Salvia* has a TLC chromatographic fingerprint substantially as illustrated in FIG. 2 or a HPLC fingerprint substantially as illustrated in FIG. 6.

16. A botanical drug or dietary supplement as claimed in claim 13 wherein the standardized extract of *Salvia* is a dark red powder which has:
   (i) no less than 1.5% by weight Tanshinone IIA by HPLC;
   (ii) a total ash content of no more than 5% by weight;
   (iii) an acid insoluble ash content of no more than 2% by weight; and
   (iv) a microbial total viable aerobic count of no more than of 1000 cfu/g.

17. A botanical drug or dietary supplement as claimed in claim 1 wherein the extract from *Schisandra* is standardized against a marker of Schizandrol A.

18. A botanical drug or dietary supplement as claimed in claim 17 wherein the extract from *Schisandra* comprises at least 2.0% by weight Schizandrol A using HPLC.

Figure 3:
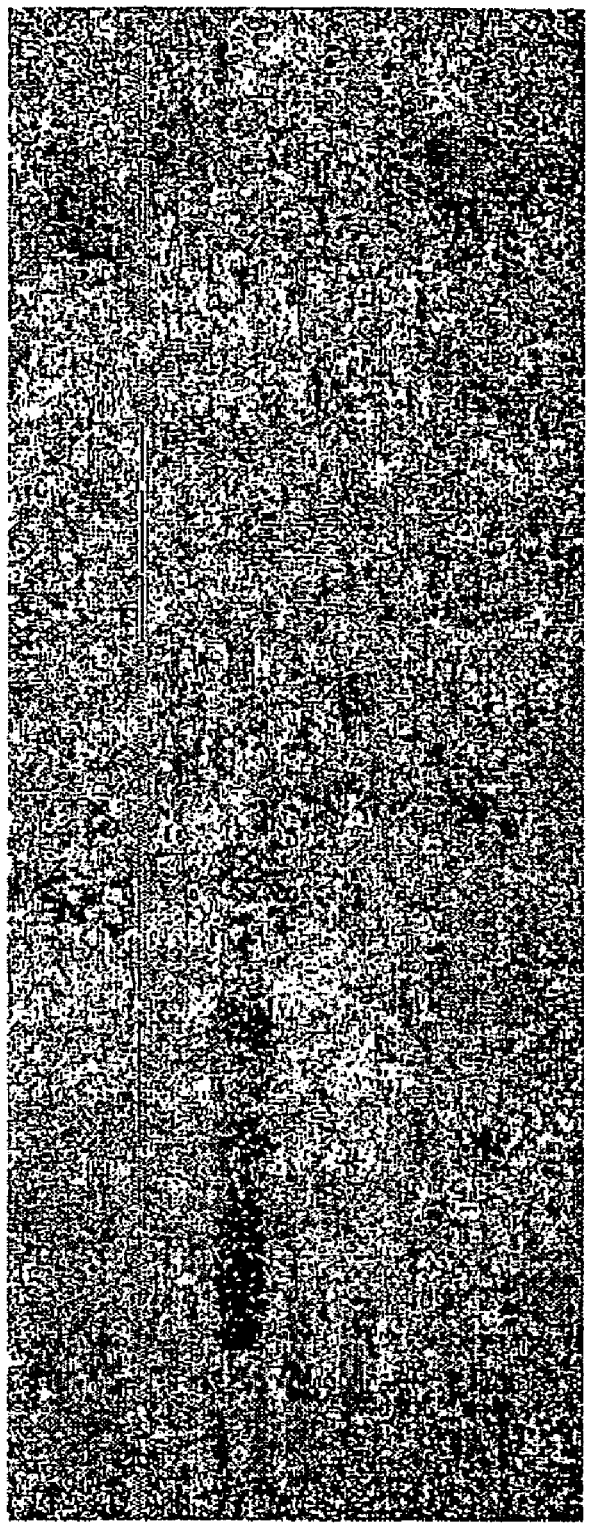
FIG. 3 is a TCL picture of the BDS of *Schisandra chinensis.*

19. A botanical drug or dietary supplement as claimed in claim 17 wherein the extract from *Schisandra* has a TLC chromatographic fingerprint substantially as illustrated in FIG. 3 or a HPLC fingerprint substantially as illustrated in FIG. 8.

20. A botanical drug or dietary supplement as claimed in claim 18 wherein the standardized extract of *Schisandra* is a brownish red powder which has:
   (i) no less than 2.0% by weight Schizandrol A;
   (ii) a total ash content of no more than 5% by weight;
   (iii) an acid insoluble ash content of no more than 2% by weight; and
   (iv) a microbial total viable aerobic count of no more than of 1000 cfu/g.

21. A botanical drug or dietary supplement as claimed in claim 1 wherein each extract is a dried ethanolic extract.

22. A botanical drug or dietary supplement as claimed in claim 1 which is provided in a unit dosage form.

23. A botanical drug or dietary supplement as claimed in claim 22 wherein the extracts are a suspension powder mixture.

24. A botanical drug or dietary supplement as claimed in claim 1 further including as excipients:
   (a) at least one gellant or thickener comprising at least one xanthum gum having a particle size distribution such that 100% by weight of the particles pass a 60 mesh sieve, 95% by weight of the particles pass a 80 mesh sieve and 70% by weight of the particles pass a 200 mesh sieve,
   (b) at least one filler; and
   (c) at least one wetting agent and or surfactant.

25. A botanical drug or dietary supplement as claimed in claim 24 wherein the xanthan gum has a molecular weight of from $3.5 \times 10^6$ to $4.0 \times 10^6$.

26. A botanical drug or dietary supplement as claimed in claim 24 wherein the wetting agent is a polyethylene glycol or macrogol.

27. A botanical drug or dietary supplement as claimed in claim 22 further including one or more of a disintegrating agent, a lubricant, a sweetening agent, a flavouring agent and a viscosifying agent.

28. A botanical drug or dietary supplement as claimed in claim 22 wherein the extracts are packaged in a sachet.

29. A botanical drug or dietary supplement as claimed in claim 22 which is packaged in a dispensing container.

30. A botanical drug or dietary supplement as claimed in claim 29 wherein the dispensing container has a sealable lid.

31. A botanical drug or dietary supplement as claimed in claim 1 wherein said extracts are in the following unit doses:
   (i) 0.200 g to 0.250 g of the *Silybum* extract;
   (ii) 0.585 g to 1.95 g of the *Astragalus* extract;
   (iii) 0.225 g to 0.375 g of the *Salvia* extract; and
   (iv) 0.150 g to 0.600 g of the *Schisandra* extract.

32. A method of treating a patient to reduce or alleviate the symptoms of Hepatitis, paticulary Hepatitis C, comprising administering to the patient an efficacious dossage of the botanical drug or dietary supplement as claimed in claim 1.

33. A method of treating a patient to reduce or alleviate the symptoms of Hepatitis, particularly Hepatitis C, comprising administering to the patient an efficacious dosage of the botanical drug or dietary supplement as claimed in claim 1 in combination with another drug, said another drug being present in an amount efficacious to reduce or alleviate the symptoms of Hepatitis, Hepatitis C, or to support healthy liver function.

34. The method as claimed in claim 33 wherein said another drug is interferon.

* * * * *

UNITED STATES PATENT AND TRADEMARK OFFICE
CERTIFICATE OF CORRECTION

PATENT NO. : 7,422,760 B2  Page 1 of 1
APPLICATION NO. : 10/589738
DATED : September 9, 2008
INVENTOR(S) : Shouming Zhong and Hongwen Yu It is certified that error appears in the above-identified patent and that said Letters Patent is hereby corrected as shown below:

Column 9, Line 25, should read as follows: -- formulated into tablets, capsules, syrups, elixirs, enteral for- --

Column 16, Line 15, should read as follows: -- the BDS of *Salvia miltiorrhiza*. The left is the BDS sample and --

Claim 32
Column 20, Line 50, should read as follows: -- symptoms of Hepatitis, particularly Hepatitis C, comprising --

Claim 32
Column 20, Line 51, should read as follows: -- administering to the patient an efficacious dosage of the --

Signed and Sealed this

Second Day of December, 2008

JON W. DUDAS
*Director of the United States Patent and Trademark Office*